United States Patent [19]

Ribaudo et al.

[11] 4,258,224
[45] Mar. 24, 1981

[54] PROCESS FOR RECOVERING TNT ISOMERS

[75] Inventors: Charles Ribaudo, Somerville; John F. Leccacorvi, Oak Ridge; Everett E. Gilbert, Morristown, all of N.J.

[73] Assignee: The United States of America as represented by the Secretary of the Army, Washington, D.C.

[21] Appl. No.: 107,194

[22] Filed: Dec. 26, 1979

[51] Int. Cl.$^3$ ............................................. C07G 79/10
[52] U.S. Cl. ..................................................... 568/935
[58] Field of Search ................................. 568/934, 935

[56] References Cited

U.S. PATENT DOCUMENTS

| | | | |
|---|---|---|---|
| 2,874,196 | 2/1959 | Norell | 568/934 |
| 3,949,008 | 4/1976 | Rosenblatt et al. | 568/935 |
| 3,956,409 | 4/1976 | Gilberg | 568/935 |
| 4,003,953 | 1/1977 | Gilbert | 568/934 |

*Primary Examiner*—Leland A. Sebastian
*Attorney, Agent, or Firm*—Nathan Edelberg; Robert P. Gibson; Harold H. Card, Jr.

[57] ABSTRACT

A process for recovering pure 2,4,6-trinitrotoluene (TNT) from a crude TNT mixture containing unsymmetrical TNT isomers which comprises forming a homogeneous powder of the crude TNT and silica gel, introducing said powder at the top of a silica gel packed column, and resolving the TNT mixture into its component isomers by contacting said powder with a developing solvent system which is not reactive with the component isomers selected from the group consisting of polar organic solvents, non-polar organic solvents, and mixtures thereof having an energy of adsorption adequate to selectively adsorb the individual TNT isomers, such as a mixture of polar acetonitrile and non-polar trichloro trifluoroethane.

10 Claims, No Drawings

PROCESS FOR RECOVERING TNT ISOMERS

DEDICATORY CLAUSE

The invention described herein may be manufactured, licensed, and used by or for the Government for governmental purposes without the payment to us of any royalty thereon.

BACKGROUND OF THE INVENTION

This invention relates to the purification of TNT (2,4,6-trinitrotoluene, also called α-TNT) for military use through a process of removing the unsymmetrical 2,4,5- and 2,3,4-isomers from TNT (containing approximately 4% unsymmetrical isomers) conventionally manufactured by nitration processes from toluene and mixed nitric and sulfuric acids.

Standard industrial procedures for removing these isomeric impurities are to treat the crude TNT with hot aqueous sodium sulfite ("sellite") which reacts with the reactive nitro groups in the meta(3) position and produces a waste sellite solution containing a mixture of sodium 2,4-dinitrotoluene-3 and 5 sulfonates. This process, however, results in a very concentrated and intensely reddish colored solution, the disposal of which is both costly and a serious water pollutant.

Purification of TNT has also been accomplished by treatment of crude TNT with aqueous ammonium sulfite and ammonium bisulfite through the process described in U.S. Pat. No. 3,956,409 to Everett Gilbert, heating crude TNT with an aqueous mixture of magnesium sulfite and magnesium bisulfite as described in U.S. Pat. No. 4,003,953 to Everett Gilbert and through purification of crude dinitrotoluene intermediate by extraction with $C_3$–$C_8$ alkanes prior to nitration, as described in U.S. Pat. No. 3,949,008 to David H. Rosenblatt et al. These procedures, while achieving acceptable levels of isomer removal, have still presented problems of disposal and have generally been time-consuming, uneconomical processes.

One procedure for purifying TNT which has been considered promising is the recrystallization of TNT from nitric acid used by A. B. Bofors in Sweden, as described in their U.S. Pat. No. 2,874,196. A major problem which has limited the widespread adaption of the nitric acid crystallization process is the disposal of the intendant alpha TNT and unsymmetrical isomer mixture obtained in the filtrate from the recrystallization. This mixture, known as "Isotrioil," has been used to some extent in commercial dynamite production, but this is not an economically viable mode of disposal in this country where supply of Isotrioil far exceeds commercial demand. Destruction of the Isotrioil by burning is technically feasible, but is also an uneconomical solution since at least half of the mixture comprises the desired alpha isomer. Proposed recover of alpha isomer by a "sweating" procedure is both time-consuming and yields an impure product.

The instant invention provides for purification of Isotrioil by adsorption and removal of the unsymmetrical 2,4,5- and 2,3,4-isomers by passing a solution thereof in a developing solvent system comprising polar and non-polar organic solvents, such as 1,1,2-trichloro-1,2,2-trifluoroethane and acetonitrile, through a column packed with silica gel.

SUMMARY OF THE INVENTION

A process for purifying a mixture of trinitrotoluene (TNT) isomers consisting essentially of alpha TNT isomer and unsymmetrical 2,4,5- and 2,3,4-isomer impurities comprising the steps of mixing said isomer mixture with a silica gel polar chromatographic adsorbent to form a paste, drying said paste to a powder, forming said powder into the form of a plug at the top of a column packed with silica gel, resolving the TNT isomer mixture in the plug by addition of a developing solvent system which will not react with isomers, selected from the group consisting of polar organic solvents, non-polar organic solvents and mixtures thereof wherein the individual component isomers will be selectively adsorbed within distinct portion of silica gel within the column, and extracting the individual components from said silica gel by means of a solvent. In the preferred embodiment, the developing solvent comprises a mixture of 1,1,2-trichloro-1,2,2-trifluoroethane and acetonitrile, the α-TNT isomer is separated from the isomer mixture by elution from the column and the unsymmetrical isomers remaining on the silica gel absorbent are extracted with a solvent, e.g., acetone.

It is the principal object of the present invention to provide a novel process for removing unsymmetrical isomers of trinitrotoluene (TNT) from TNT to yield a purer military grade explosive.

It is a further object of the invention to provide an economical process for purifying crude TNT whereby a superior recovery of TNT is achieved with substantially complete removal of unsymmetrical TNT isomers.

A still further object of this invention is to provide an economical process for disposal of a mixture of alpha TNT and unsymmetrical isomers obtained from the filtrate of the nitric acid recrystallization of crude TNT whereby problems of pollution are substantially eliminated.

Another object of this invention is to provide a process for separating mixtures of TNT isomers by means of passing the isomer mixture through a column packed with silica gel polar chromatographic adsorbent through use of a developing solvent system consisting of polar organic solvent, non-polar organic solvents and mixtures thereof.

These and other objects of the invention will become apparent from the following detailed description.

DETAILED DESCRIPTION OF THE INVENTION

In accordance with the process of the present invention, the foregoing and other objects can be achieved by the steps of mixing the crude TNT isomer mixture with silica gel to form a paste, completely drying said paste to a powder and forming said powder into a "plug" at the top of a silica gel packed column, and subsequently resolving the isomer mixture in the column by addition of a developing solvent consisting essentially of a polar organic solvent, a non-polar organic solvent or mixture thereof. The component TNT isomers, which have separated in the column, are monitored by irradiating the column with ultraviolet radiation (254 nm). The separated TNT isomers appear as dark bands against the green fluorescent background. Other forms of visualization or monitoring techniques can be used to follow the migration of the isomers in the column. The α-TNT is eluted from the column during the development, leaving the unsymmetrical isomers in the column at the end of the development. These isomers can be recorded by removing the silica gel in the column, portionwise, with each band subsequently being extracted with acetone. Evaporation of the eluent and acetone solvents will give the pure TNT isomers, with the positions taken by the isomers on the column, starting from the bottom of the column, being the 2,4,6-(alpha) isomer and then the respective unsymmetrical 2,4,5- and 2,3,4-isomers.

The silica gel used in the process of this invention for separation of TNT isomers in Isotrioil mixtures resulting from the nitration of the toluene is a typical polar chromatographic adsorbent. The silica gel surface is characterized by the presence of hydroxyl groups which serve as the adsorption sites. Silica gel is a porous material which, for the practice of this invention, preferably has a surface area between 300-600 $m^2/g$ and a pore diameter between 100-200 Å (Angstroms). Silica having larger or smaller surface area and pore diameter can also be used, with increasing particle size resulting in increased flow rates of the solvent system mixture in the column. The essential features of the silica gel adsorbent are its surface structure, absorption sites and sample selectivity characteristics for TNT isomers. Other adsorbents, like alumina, used in columns under pressure, could be used if they exhibited similar adsorbent characteristics to that of silica.

The developing solvent system used in the process of this invention is preferably a mixture of a polar solvent acetonitrile and the non-polar saturated hydrocarbon trichloro trifluoroethane. The essential solvent properties of these solvents are characterized by their energy of adsorption. Any mixture of a non-polar and polar solvent or a single solvent exhibiting an energy of adsorption similar to that of the preferred developing system could be used for the separation of TNT isomers in the process of this invention. Thus a developing solution of hexane and methylene chloride or cyclohexane and ethyl acetate can be used. The following table of common solvents in order of increasing energy of adsorption, as measured on alumina, can be used to estimate the relative energy of adsorption on silica gel since the order of adsorption is essentially the same on silica gel as on alumina.

| Solvent | $5°(Al_2O_3)$ |
| --- | --- |
| Fluoroalkanes | −0.25 |
| n-Pentane | 0.00 |
| Hexane | 0.00 |
| Isooctane | 0.01 |
| Petroleum ether Skellysolve B, etc. | 0.01 |
| n-Decane | 0.04 |
| Cyclohexane | 0.04 |
| Cyclopentane | 0.05 |
| Diisobutylene | 0.06 |
| I-Pentente | 0.08 |
| Carbon disulfide | 0.15 |
| Carbon tetrachloride | 0.18 |
| Amyl chloride | 0.26 |
| Butyl chloride | 0.26 |
| Xylene | 0.26 |
| i-Propyl ether | 0.28 |
| i-Propyl chloride | 0.29 |
| Toluene | 0.29 |
| n-Propyl chloride | 0.30 |
| Chlorobenzene | 0.30 |
| Benzene | 0.32 |
| Ethyl bromide | 0.37 |
| Ethyl ether | 0.38 |
| Ethyl sulfide | 0.38 |
| Chloroform | 0.40 |

-continued

| Solvent | $5°(Al_2O_3)$ |
| --- | --- |
| Methylene chloride | 0.42 |
| Methyl-i-butylketone | 0.43 |
| Tetrahydroufurane | 0.45 |
| Ethylene dichloride | 0.49 |
| Methylethylketone | 0.51 |
| I-Nitropropane | 0.53 |
| Acetone | 0.56 |
| Dioxane | 0.56 |
| Ethyl acetate | 0.58 |
| Methyl acetate | 0.60 |
| Amyl alcohol | 0.61 |
| Dimethyl sulfoxide | 0.62 |
| Nitromethane | 0.64 |
| Acetonitrile | 0.65 |
| Butyl cellusolve | 0.74 |
| i-propanol, n-propanol | 0.82 |
| Ethanol | 0.88 |
| Methanol | 0.95 |
| Ethylene glycol | 1.11 |
| Acetic acid | Large |
| Water | Larger |
| Salts & Buffers | Very large |

Acetonitrile, with an energy of adsorption, $E^o(Al_2O_3)$ of 0.65 is grouped with other polar organic solvents such as methyl and ethyl acetates, acetone, dioxane, nitropropane and others within an $E^o(Al_2O_3)$ range of 0.29 to 1.0 that have been found to be useful developing solvents within the practice of this invention. Exceptions to the listed solvents within the energy of adsorption range are the amines, such as pyridine, diethylamine and aniline, which are reactive with TNT isomers. Trichloro trifluorethane, though not listed, would be among the non-polar, saturated organic solvents such as fluoroalkane, N-pentane, hexane, isooctane and other exhibiting $E^o(Al_2O_3)$ between −0.25 and 0.05 which can be used in the developing solvent mixture of this invention.

It is a critical part of the separation procedure of this invention that a relatively large sample of the Isotrioil TNT isomer mixture be placed in the silica gel packed column in a uniform manner without channeling or forming irregular and overlapping zones in the column. Applicants have developed a unique means of assuring uniform addition of the isomer mixture to the column by means of introducing the Isotrioil sample in the form of a "plug" prepared by packing the top of a column with a powder of Isotrioil and silica gel. Specifically, Isotrioil and silica gel are mixed into a paste with acetone and the paste is subsequently dried to give a homogeneous powder which is placed on top of the silica gel in the column while the column is under vacuum, to form the novel "plug."

The process of the present invention can be best illustrated by the following examples of the preferred embodiment of carrying out the process of purifying mixtures of TNT isomers.

EXAMPLE 1

A 30×2.4 cm quartz tube was packed with 53 g of a mixture of 98% silica gel (available commercially from Gelman Instrument Co.) and 2% zinc silicate fluorescent indicator. One half gram of "synthetic Isotrioil" was then prepared from pure TNT isomers, wherein the mixture comprised 50% 2,4,6-TNT, 34% 2,4,5-TNT and 16% 2,3,4-TNT isomers. The mixture, with 5 g added pure silica gel, was made into a paste with acetone. The paste was thoroughly dried, and the resulting powder was introduced into the column by being placed on the top of the silica gel packed in the tube while the other end of the column was under vacuum, forming a "plug." The Isotrioil was then resolved on the column by adding to the top of the column, 400 ml of a chromatographic developing solution comprising 97.5% 1,1,2-trichloro-1,2,2-trifluoroethane (commercially available under the trademark "Genesol 113" ™, b.p. 48° C.) and 2.5% acetonitrile, while the other end of the column was under vacuum, over a four-hour period. Component separation was monitored by irradiating the column with ultraviolet radiation (254 nm). The separated isomers appear as dark bands against a green fluorescent background provided by the zinc silicate fluorescent indicator. After the 2,4,6-TNT band had migrated and eluted from the column, each band containing the respective unsymmetrical isomers, was extracted with acetone. Evaporation of the eluent and acetone solvents gave the pure TNT isomers, as confirmed by gas chromatographic analysis. The positions taken by the isomers on the column, starting from the bottom, i.e., the order of elution to last, were as follows:

2,4,6-TNT (alpha TNT); 2,4,5-TNT and 2,3,4-TNT

EXAMPLE 2

One part of crude TNT was dissolved at 85° C. in 3.6 parts 61% nitric acid. The solution was stirred 2.2. hours at 35° C. to effect crystallization of the 2,4,6-(alpha) TNT isomer, which was recovered by filtration. The filtrate was then distilled, yielding the nitric acid for recycles to the crystallization step, and about 8% of the original crude TNT as Isotrioil. The Isotrioil was then separated on a silica gel packed column in accordance with the procedure described in Example 1. Excellent resolution was obtained into the three pure TNT isomers. The recovered alpha isomer was combined with that previously recovered in the crystallization step. The 2,4,5- and 2,3,4-TNT unsymmetrical isomers can, for example, be converted into the explosives "m-methyltetryl," and trinitro-m-cresol by the processes described in T. L. Davis, *The Chemistry of Powder and Explosives*, p. 147.

The procedures described in the above examples can be varied considerably to include the use of other developing solutions such as a mixture of hexane and methylene chloride or a mixture of cyclohexane and ethyl acetate, and other solvents having a polarity similar to that of the preferred developing solvent mixture. The size of the silica particles may also be varied in the process of this invention. In particular, the use of larger particle size silica than silica gel would permit faster flow of the solvent mixture and would eliminate the need for the zinc silicate indicator when monitoring is not required. The faster flow rate would also permit more rapid, complete separation of the alpha TNT without removing the adsorbent from the column since alpha TNT moves downward more rapidly than the other two unsymmetrical TNT isomers.

The specific amounts of developing solvent used in the process of this invention are not critical and can be varied considerably from that illustrated in the examples. Sufficient solvent should of course be used to completely resolve the component isomers and amounts substantially in excess of that illustrated would not be advisable due to excessive disassociation and loss of the desired alpha-TNT isomer.

The size of the separator column and the amount of silica gel adsorbent used in the process of this invention is dependent upon the amount of TNT isomer to be separated, with increasing amounts of adsorbent, i.e., increased amounts of adsorbent sites being needed to separate larger quantities of isomers.

It is a critical aspect of this invention that sufficient active adsorbent sites be provided to avoid "overloading" of the packed column, since the more rapidly separating isomers will trail or stream into the zones where less rapidly separating isomers would otherwise be adsorbed. The overlapping of zones resulting from overloading in turn reduces the efficiency of the separation method of this invention. Optimization of the column and amount of adsorbent required for separation of a given quantity of TNT-isomer mixture in accordance with conventional chromographic separation procedure would be obvious to one skilled in the art to avoid problems of overloading.

The particular details of construction of the apparatus used in the process of this invention are not critical and can be selected from a wide range of conventional columns, separators, etc. Similarly, the reaction condition of temperature and pressure illustrated can be varied within the skill of one in the art to obtain optimum yield of component TNT isomers.

Though the use of silica gel as a chromatographic adsorbent is preferred, one skilled in the art could obviously use other adsorbents, e.g., alumina under pressure, provided these adsorbents possessed similar surface structure, adsorption sites and sample selectivity to that of silica gel.

The essential features of this invention are the use of a silica gel adsorbent with a developing solvent system that is relatively non-reactive with TNT-isomers and which exhibits an acceptable energy of adsorption, i.e., the same order of that possessed by the mixture of polar acetonitrile and non-polar trichloro trifluorethane. Another essential feature of this invention is the formation of a homogeneous TNT-isomer-silica gel powder, e.g., a plug for uniform introduction of the TNT isomer mixture, e.g., Isotrioil into the silica gel packed column.

The foregoing disclosure is merely illustrative of the principles of this invention and are not to be interpreted in a limited sense. Applicants do not desire to be limited to the exact details of construction shown and described since obvious modifications will occur to a person skilled in the art.

We claim:

1. A process for purifying a mixture of trinitrotoluene (TNT) isomers consisting essentially of α-TNT isomer, as a major constituent, and unsymmetrical 2,4,5- and 2,3,4-isomers comprising the steps of uniformly introducing the isomer mixture into an absorbent packed column and separating said mixture into its isomers in said column through use of a developing solvent system in which the isomers are soluble and separating the component isomer from the absorbent within the column.

2. The process of claim 1 wherein the absorbent used within the column is silica gel.

3. The process of claim 2 wherein the developing solvent system is selected from the group consisting of polar organic solvents, non-polar organic solvents, and mixtures thereof.

4. The process of claim 3 wherein the developing solvent solution is a mixture of a polar solvent having an $E^o(Al_2O_3)$ in the range of 0.29 to 1.0 and a non-polar solvent having an $E^o(Al_2O_3)$ between $-0.25$ and $0.05$.

5. The process of claim 4 wherein the developing solvent is a mixture of polar acetonitrile and non-polar trichloro trifluoroethane.

6. The process of claim 2 wherein the isomer mixture is uniformly introduced into the column by means of a homogeneous powder prepared by mixing said isomer mixture with silica gel in acetone to form a paste and drying the paste to said powder.

7. The process of claim 6 wherein the powder is placed on top of the silica gel in the column, while the column is under vacuum, to form a plug at the top of the column.

8. The process of claim 5 wherein the developing solution comprises 97.5% by volume 1,1,2-trichloro-1,2,2-trifluoroethane and 2.5% acetonitrile.

9. The process of claim 2 wherein the adsorbent comprises 98% silica gel and 2% of a zinc silicate fluorescent indicator which is used to monitor component isomer separation in the column.

10. The process of claim 9 wherein the component TNT isomers are deposited portionwise in the column, starting from the bottom, as the respective pure isomer 2,4,6 (alpha)-TNT, B 2,4,5-TNT and 2,3,4-TNT and the respective portions of silica gel containing the respective isomers are extracted with acetone to yield the pure TNT isomer.

* * * * *